United States Patent [19]

Gauri

[11] 4,017,626
[45] Apr. 12, 1977

[54] FUNGICIDALLY ACTIVE URACIL DERIVATIVES

[75] Inventor: Kailash Kumar Gauri, Lentfohrden, Germany

[73] Assignee: Robugen GmbH, Pharmazeutische Fabrik, Esslingen, Germany

[22] Filed: Jan. 14, 1975

[21] Appl. No.: 541,047

[30] Foreign Application Priority Data

Jan. 14, 1974 Germany .......................... 2401619

[52] U.S. Cl. ................................. 424/251; 260/260
[51] Int. Cl.² ........................................ A01N 9/22
[58] Field of Search .................... 260/260; 424/251

[56] References Cited

UNITED STATES PATENTS 3,235,363 2/1966 Luckenbaugh .................... 260/260

FOREIGN PATENTS OR APPLICATIONS 1,177,874 1/1970 United Kingdom ............... 260/260

*Primary Examiner*—Paul M. Coughlan, Jr.
*Attorney, Agent, or Firm*—Birch, Stewart, Kolasch and Birch

[57] ABSTRACT

Uracil derivatives having the general formula:

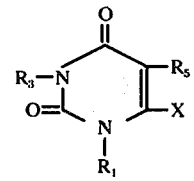

wherein $R_1$ and $R_3$ are each an alkyl group of 2 to 10 carbon atoms or an alkenyl group of 3 to 10 carbon atoms, $R_5$ is an alkyl group of 2 to 5 carbon atoms and X is a hydrogen or halogen atom. These compounds are characterized by their fungicidal activity.

4 Claims, No Drawings

FUNGICIDALLY ACTIVE URACIL DERIVATIVES

This invention relates to novel uracil derivatives. More particularly, it relates to novel uracil derivatives having fungicidal activity and to a process for preparing the same.

The uracil derivatives of the present invention have the following general formula:

(I)

In general, the compounds of the invention can be prepared in accordance with the following procedure. One mol of a uracil derivative having the general formula (II) is dissolved in water-free acetone and heated under reflux for about 24 hours with 1.5 mols of an alkyl halide having 2 to 10 carbon atoms, such as ethyl chloride, butyl bromide, decyl chloride or the like in the presence of one mol of water-free potassium carbonate. After filtration of the reaction mixture, the filtrate is concentrated under vacuum and the desired uracil compound is separated by distillation.

The characteristic data of the compounds according to the invention are shown in the following Table.

TABLE I

| No. | Substance | Molecular Weight | UV - BANDS max₁ | max₂ | min | | ANALYSIS C | H | N | Cl | O |
|---|---|---|---|---|---|---|---|---|---|---|---|
| 1 | 1-crotyl-3,5-diethyl-6-chlorouracil | 256.74 $C_{12}H_{17}N_2O_2Cl$ | a 218 b 218 c 218 | 276 276 276 | 242 242 242 | Calculated % Found % | 56.13 55.97 | 6.67 6.59 | 10.91 10.95 | 13.81 | 12.46 |
| 2 | 1-propyl-3,5-diethyl-6-chlorouracil | 244.72 $C_{11}H_{17}N_2O_2Cl$ | a 218 b 218 c 217 | 270 270 272 | 242 242 242 | Calculated % Found % | 53.98 54.01 | 7.00 6.98 | 11.44 11.35 | 14.80 14.80 | 13.07 |
| 3 | 1-butyl-3,5-diethyl-6-chlorouracil | 257.73 $C_{12}H_{19}N_2O_2Cl$ | a 240 b 240 c 240 | 294 294 294 | 270 270 270 | Calculated % Found % | 55.91 55.32 | 7.44 7.41 | 10.94 11.87 | 13.76 12.87 | 12.41 |
| 4 | 1-pentyl-3,5-diethyl-6-chlorouracil | 270.74 $C_{13}H_{21}N_2O_2Cl$ | a 216 b 216 c 222 | 274 274 274 | 242 242 244 | Calculated % Found % | 57.66 56.87 | 7.75 7.70 | 10.34 10.83 | 13.09 12.67 | 11.81 |
| 5 | 1-hexyl-3,5-diethyl-6-chlorouracil | 283.75 $C_{14}H_{23}N_2O_2Cl$ | a 214 b 214 c 214 | 274 274 274 | 240 240 240 | Calculated % Found | 59.92 58.24 | 8.10 7.98 | 9.87 10.06 | 12.49 11.98 | 11.27 |
| 6 | 1-heptyl-3,5-diethyl-6-chlorouracil | 296.76 $C_{15}H_{25}N_2O_2Cl$ | a 216 b 216 c 216 | 276 274 274 | 242 242 242 | Calculated % Found % | 60.70 60.10 | 8.71 8.41 | 9.44 9.88 | 11.94 11.38 | 10.77 | a = neutral
b = acid
c = alkaline

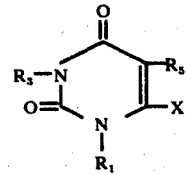

wherein $R_1$ and $R_3$ are each an alkyl group of 2 to 10 carbon atoms or an alkenyl group of 3 to 10 carbon atoms, $R_5$ is an alkyl group having 2 to 5 carbon atoms and X is a hydrogen or halogen atom.

These uracil derivatives are obtained according to the invention by the alkylation of a uracil derivative having the following general formula:

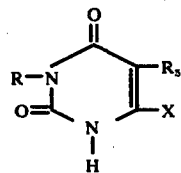

(II)

wherein R is a hydrogen atom or an alkyl group of 2 to 10 carbon atoms, $R_5$ is an alkyl group having 2 to 5 carbon atoms and X is a hydrogen or halogen atom.

Accordingly, a primary objective of the invention is to provide novel uracil derivatives having fungicidal activity. Another object of the invention is to provide a process for preparing these uracil compounds.

These and other objects and advantages of the present invention will become apparent to those skilled in the art from a consideration of the following specification and claims.

In accordance with the above-described method of preparation, the following exemplary compounds falling within the scope of formula (I) are prepared:

1-decyl-3-ethyl-5-butyl-6-chlorouracil
1-butyl-3-decyl-5-propyl-6-chlorouracil
1-pentenyl-3-butyl-5-butyl-6-chlorouracil
1-heptenyl-3-octyl-5-ethyl-6-chlorouracil
1,3-dipentenyl-5-ethyl-6-chlorouracil In the following Table II, the value of the fungicidal activity of a number of compounds according to the invention is set forth.

TABLE II

| | | | | Diameter of the inhibiting zone mm. at 0.005M concentration with respect to the stem | | | |
|---|---|---|---|---|---|---|---|
| $R_1$ | $R_3$ | $R_5$ | X | I | II | III | IV |
| Propyl | Ethyl | Ethyl | Cl | 60 | 60 | 52 | 56 |
| Butyl | Ethyl | Ethyl | Cl | 54 | 52 | 48 | 44 |
| Pentyl | Ethyl | Ethyl | Cl | 50 | 34 | 34 | 44 |
| Hexyl | Ethyl | Ethyl | Cl | 38 | 0 | 16 | 26 |
| Heptyl | Ethyl | Ethyl | Cl | 40 | 0 | 0 | 16 |

I Trichophyton rubrum
II Trichophyton mentagrophytes
III Microsporum gypseum

TABLE II-continued

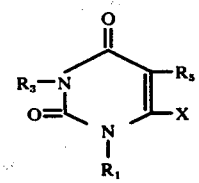

| | | | | Diameter of the inhibiting zone mm. at 0.005M concentration with respect to the stem | | | |
|---|---|---|---|---|---|---|---|
| $R_1$ | $R_3$ | $R_5$ | X | I | II | III | IV |

IV Epidermophyton floccosum

As Table II shows, the uracil derivatives according to the invention possess a high degree of activity against various dermatophytes. It is of particular note that heretofore no uracil derivatives were known which exhibited fungicidal activity. This feature of the present invention is completely novel and unobvious.

As noted above, the uracil derivatives of the present invention possess fungicidal activity. They may be used alone in such utility, but from a more practical point of view, they are usually extended with a suitable inert carrier or diluent, if desired, by the aid of any emulsifier to formulate a preparation as is conventionally employed in this art such as pellets, dust, wettable powder, or an emulsifiable concentrate. Examples of the solid carrier or diluent are talc, bentonite, clay, kaolin, diatomaceous earth, vermiculite, etc.. Examples of the liquid carrier or diluent are benzene, xylene, alcohols, ethers, and other inert organic liquids as are commonly employed in the art. As the emulsifier, there may be employed alkyl sulfates, alkyl sulfonates, aryl sulfonates, polyethyleneglycol ethers, polyvalent alcohol esters and the like. When desired, the preparation may contain any other active ingredient such as an insecticide, a herbicide or a fertilizer.

Fungicidally active amounts of the uracil derivatives of the invention may be employed in such preparations, and these amounts can be readily determined by one skilled in the art with regard to the desired effect and result.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A fungicidal composition for inhibiting the growth of dermatophytes comprising an amount effective to inhibit the growth of dermatophytes of a uracil derivative having the formula:

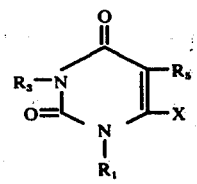

wherein $R_1$ and $R_3$ are each an alkyl group of 2 to 10 carbon atoms, $R_5$ is an alkyl group having 2 to 5 carbon atoms and X is a chlorine atom, and an inert carrier.

2. A method for inhibiting the growth of dermatophytes which comprises contacting the dermatophytes with an effective dermatophyte-inhibiting amount of a uracil derivative having the formula:

wherein $R_1$ and $R_3$ are each an alkyl group of 2 to 10 carbon atoms, $R_5$ is an alkyl group having 2 to 5 carbon atoms and X is a chlorine atom, and an inert carrier.

3. The method of claim 2, wherein said uracil derivative is selected from the group consisting of:

1-propyl-3,5-diethyl-6-chlorouracil
1-butyl-3,5-diethyl-6-chlorouracil
1-pentyl-3,5-diethyl-6-chlorouracil
1-hexyl-3,5-diethyl-6-chlorouracil and
1-heptyl-3,5-diethyl-6-chlorouracil.

4. The method of claim 2, wherein said uracil derivative is 1-propyl-3,5-diethyl-6-chlorouracil.

* * * * *